(12) United States Patent
Tijs et al.

(10) Patent No.: US 10,035,026 B2
(45) Date of Patent: Jul. 31, 2018

(54) SYSTEM AND METHOD FOR RADIOTHERAPEUTIC TREATMENT

(71) Applicant: KONINKLIJKE PHILIPS N.V., Eindhoven (NL)

(72) Inventors: Tim Johannes Willem Tijs, Stramproy (NL); Laura Klaming, Utrecht (NL); Juergen Vogt, Eindhoven (NL); Daisy Van Minde, Eindhoven (NL); Björn Nicolaas Servatius Vlaskamp, 'sHertogenbosch (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/418,652

(22) PCT Filed: Aug. 5, 2013

(86) PCT No.: PCT/IB2013/056404
§ 371 (c)(1),
(2) Date: Jan. 30, 2015

(87) PCT Pub. No.: WO2014/024115
PCT Pub. Date: Feb. 13, 2014

(65) Prior Publication Data
US 2015/0196780 A1    Jul. 16, 2015

Related U.S. Application Data

(60) Provisional application No. 61/681,256, filed on Aug. 9, 2012.

(51) Int. Cl.
*A61N 5/10* (2006.01)

(52) U.S. Cl.
CPC .......... *A61N 5/1049* (2013.01); *A61N 5/1069* (2013.01); *A61N 2005/1059* (2013.01); *A61N 2005/1074* (2013.01)

(58) Field of Classification Search
CPC ................. A61N 2005/105–2005/1098; A61N 5/103–5/1084
See application file for complete search history.

(56) References Cited

U.S. PATENT DOCUMENTS

| 5,446,548 A | * | 8/1995 | Gerig | ........................ | A61B 6/08 250/462.1 |
| 6,143,003 A | * | 11/2000 | Cosman | ............... | A61B 6/0421 128/846 |

(Continued)

OTHER PUBLICATIONS

Clover, K. et al. "Disruption to radiation therapy sessions due to anxiety among patients receiving radiation therapy to the head and neck area can be predicted using patient self-report measures". Psychooncology, 2011; 20 (12):1334-41.

(Continued)

*Primary Examiner* — Catherine B Kuhlman

(57) ABSTRACT

A system and method for radiotherapeutic treatment of a patient (20) are provided. The system comprises a patient carrier (11) for receiving the patient (20), means for monitoring (12) positions of at least two different body parts of the patient (20), a processor (14) and feedback means (13). The processor (14) is coupled to the means for monitoring (12) positions and is operative to analyze the monitored positions to determine, for each body part of the at least two body parts, a displacement of the respective body part with respect to a particular desired position. The feedback means (13) are coupled to the processor (14) for interacting with the patient (20) and to provide feedback concerning the displacement of the respective body part.

18 Claims, 3 Drawing Sheets

(56) References Cited

U.S. PATENT DOCUMENTS

| | | | |
|---|---|---|---|
| 6,279,579 B1* | 8/2001 | Riaziat | A61N 5/1049 128/897 |
| 7,204,254 B2 | 4/2007 | Riaziat et al. | |
| 8,200,315 B2 | 6/2012 | Mostafavi | |
| 8,981,324 B2 | 3/2015 | Rigney et al. | |
| 8,996,094 B2 | 3/2015 | Schouenborg et al. | |
| 9,508,145 B2 | 11/2016 | Gum et al. | |
| 2005/0283068 A1 | 12/2005 | Zuccolotto et al. | |
| 2010/0080431 A1 | 4/2010 | Datema et al. | |
| 2010/0231483 A1 | 9/2010 | Bazih et al. | |
| 2011/0249088 A1* | 10/2011 | Hannibal | A61N 5/1048 348/43 |
| 2011/0306863 A1 | 12/2011 | Koshnitsky et al. | |
| 2012/0316425 A1* | 12/2012 | Raleigh | A61B 6/12 600/411 |
| 2012/0320178 A1 | 12/2012 | Siegert et al. | |

OTHER PUBLICATIONS

Lecchi, M. et al. "Current concepts on imaging in radiotherapy", Eur J Nucl Med Mol Imaging. Apr. 2008;35(4):821-37.

* cited by examiner derlying the invention is that, if, during the course of treatment, the patient's body position is monitored, the quality of the treatment can be improved.

SYSTEM AND METHOD FOR RADIOTHERAPEUTIC TREATMENT

CROSS-REFERENCE TO PRIOR APPLICATIONS

This application is the U.S. National Phase application under 35 U.S.C. § 371 of International Application No. PCT/IB2013/056404, filed on Aug. 5, 2013, which claims the benefit of U.S. Provisional Application No. 61/681,256, filed on Aug. 9, 2012. These applications are hereby incorporated by reference herein.

FIELD OF THE INVENTION

This invention relates to a system for radiotherapeutic treatment of a patient, the system comprising a patient carrier for receiving the patient, means for monitoring the patient and a processor, coupled to the means for monitoring.

The invention further relates to a method of controlling patient movements comprising monitoring the patient.

The invention also relates to a computer program product for use in such a method.

BACKGROUND OF THE INVENTION

Radiotherapy (also known as Radiation Oncology and Radiation Therapy) is generally used as part of cancer treatment to control or kill malignant cells. Radiotherapy makes use of ionizing radiation which, damaging the DNA of exposed tissue and thereby leading to cellular death. The radiation can be delivered by a machine outside the body (external beam radiation therapy) or it can come from radioactive seeds placed into or near the tumor (internal beam radiation therapy, more commonly called brachytherapy).

External beam radiation therapy is the most frequently used form of radiotherapy and is delivered using a linear accelerator (LINAC). The linear accelerator uses microwave technology to accelerate electrons and then allows these electrons to collide with a heavy metal target. As a result of the collisions, high-energy x-rays are produced from the target. These high energy x-rays are shaped as they exit the machine to conform to the shape of the patient's tumor and the customized beam is directed to the patient's tumor.

The patient lies on a moveable treatment couch and lasers are used to make sure the patient is in the proper position. The beam comes out of a part of the accelerator called a gantry, which can be rotated around the patient. Radiation can be delivered to the tumor from any angle by rotating the gantry and moving the treatment couch. During treatment the radiation therapist continuously watches the patient through a closed-circuit television monitor. There usually is also a microphone in the treatment room so that the patient can speak to the therapist if needed. Imaging tools are checked regularly to make sure that the beam position doesn't vary from the original plan.

For effective operation of the radiotherapy system, it is necessary to include a margin of normal tissue around the tumor to allow for uncertainties in daily set-up and internal tumor motion. These uncertainties can be caused by internal movement, e.g. due to respiration. In image guided radiotherapy (IGRT), two and three-dimensional imaging is used to help better deliver radiation therapy to cancerous tumors. In, e.g., "Current concepts on imaging in radiotherapy" by Lecchi et al, MRI, PET or CT images are used for monitoring breathing motions. The article discloses three approaches for dealing with these breathing motions. In one approach, the patient is asked to hold his breath during treatment delivery for obtaining a static tumor position. When using respiratory gating, CT images are used for making it possible to only deliver treatment during well defined parts of the breathing cycle. The third approach is tumor tracking in which the 4D image data (3D+time) is used for making the treatment beam follow the tumor.

Extensive changes in body position can even cause session disruption, thereby hindering the radiotherapy workflow. Body position changes (posture/movements) can occur both voluntary and involuntary. Examples of involuntary changes include respiration (i.e., we breathe often without thinking about it), restless legs and the fact that office workers behind a PC frequently "worsen" (and then correct again) their posture throughout the day. Currently, preventive measures for patient movement/posture in radiotherapy include patient-staff communication (prior to radiotherapy, a patient is told or reminded that lying still is important) and physical support (e.g., head rest, knee rest).

Despite the preventive measures, body position related session disruption, e.g., due to patient anxiety, is a frequently reported problem in radiotherapy. For instance, Clover et al ("Disruption to radiation therapy sessions due to anxiety among patients receiving radiation therapy to the head and neck area can be predicted using patient self-report measures", Psychooncology, 2010) recently found that anxiety-related session disruption occurs in a substantial amount of radiotherapy patients: 11% duration baseline session and even 24% during treatment session 1.

In addition, a radiotherapy specific problem is that, during radiation, the LINAC gantry circles around the patient while the patient remains at steady position on the bed. This can trigger patient motion in different ways. Motion in the patient's visual field can cause a perception of self-motion (a phenomenon known as "vection"). Vection, in turn, can cause compensatory movements and anticipatory movements. In addition, vection can lead to motion sickness ("vertigo"), can also trigger undesirable patient motion. Particularly elderly persons are susceptible to vection-based self-motion.

OBJECT OF THE INVENTION

It is an object of the invention to reduce the problems related to patient movement.

SUMMARY OF THE INVENTION

According to a first aspect of the invention, this object is achieved by providing a system for radiotherapeutic treatment of a patient, the system comprising a patient carrier for receiving the patient, means for monitoring positions of at least two different body parts of the patient, a processor, coupled to the means for monitoring positions, the processor being operative to analyze the monitored positions to determine, for each body part of the at least two body parts, a displacement of the respective body part with respect to a particular desired position, and feedback means, coupled to the processor, for interacting with the patient to provide feedback concerning the displacement of the respective body part.

By dividing the body into separate segments and by providing feedback about the positions or movements of the individual segments, the ability of the patient not to disturb the treatment by detrimental changes in body position is significantly increased. The detailed feedback makes it much easier to take the desired position and to remain motionless than with the mere instruction not to move. For example, when just instructing to remain motionless it is almost impossible to prevent visually induced self-motion caused by the circling gantry. When, however, telling the patient to concentrate on a specific body part, it is easier for the patient to maintain or retain the correct posture. The detailed feedback also helps to make the patient aware of movements he was not yet aware of before. For example, the system may warn the user when he nervously taps his fingers. The overall improvement of the user's awareness of his posture and movements may reduce the amount of visually induced self-motion. The feedback may be provided to the patient directly or to a physician or operator of the system who in turn instructs the patient to make or restrain from certain movements. The patient carrier usually is a table, coach or chair-like object on which the patient is positioned in order to receive treatment. In the following, when the word table is used, it is to be noted that this is just an example of a suitable patient carrier.

The interaction may be realized by, e.g., informing the patient about the displacement of the respective body part or by moving the respective body part in order to undo the displacement. The informing of the patient may, e.g., take place via visual, acoustic or tactile means. A monitor may provide textual instructions or highlight the relevant body parts in a visual representation of the patient. Audible instructions may be provided via headphones or a speaker system. Vibrating elements may provide tactile feedback directly to the relevant body parts. The feedback means may directly inform the patient or might inform the treating physician, who interprets the information and then informs the patient. Instead of only providing information, the feedback means may be arranged for, in dependence of the detected displacement, restricting a freedom of movement for the respective body part or even for moving the respective body part to undo the displacement. This may e.g. be realized by tightening a belt, raising a dividing wall or inflating air bags.

In an embodiment, the processor is further operative to determine a need for a compensating movement of the respective body part and the feedback means are arranged for communicating the need for the compensating movement of the respective body part. The need may be communicated as a simple and instructive way, e.g. 'Move your left arm to this position'. Alternatively the need is communicated in a more gradual and warning way, e.g. 'Left arm is slightly out of position (40% of threshold value). If things get worse, you will have to move it'.

If the need for a compensating movement is communicated, the processor may further be operative to determine a desired direction of the compensating movement and the feedback means may be arranged for indicating the desired direction. The processor may further be operative to determine a desired extent of the compensating movement and the feedback means may be arranged for indicating the desired extent. For example, vibrating elements in the patient carrier may provide tactile feedback to specific body parts. By varying, e.g., a frequency of the vibration the system may indicate whether the body part is closer to or further away from the ideal position.

In a preferred embodiment, the feedback means comprise display means for displaying a body representing figure and for indicating, for each body part of the at least two body parts, the need for the compensating movement by visually highlighting a respective one of the at least two body parts in the body representing figure. When seeing his own movements, required movements or desired positions for specific body parts, the user obtains an increased control over his position. Highlighting a left leg means that the left leg should be moved. Highlighting a head means that the head should be moved. Of course, when the display is positioned opposite the patient, left and right may be interchanged in order to obtain a mirror like visualization of the patient and his movements.

In this embodiment the processor may further be operative to determine a desired extent of the compensating movement and the display means may be arranged for using color coding for indicating the desired extent. An orange arm may, e.g., indicate that a small arm movement is needed and a red arm indicates a larger movement is required. Such an indication helps the patient not to overcompensate or undercompensate the earlier undesired motion. The required direction of movement may, e.g., be indicated using arrows, a silhouette of the body part at its desired position. Also audible instructions may be used for indicating direction and extent: "Please move your left arm slightly closer to your body". Also combinations of visual and audible instructions may be used.

The system may further comprise storage means, coupled to the processor, for storing the monitored positions, the processor being arranged to use stored monitored positions for determining an impending displacement of the respective body part, the feedback means being arranged for providing feedback concerning the impending displacement of the respective body part. If the system, e.g., knows that a certain movement of the gantry will result in an undesired rotation of the head, the feedback means may already warn the user not to move his head or may even suggest a slight movement in the opposite direction. If the system knows, that a user typically overcompensates for the movements he is instructed to correct, the system may decide to communicate smaller compensating movements than actually required. The predictions may be based on stored information concerning the patient on the patient carrier himself or on general aggregated information concerning all previous patients or a subset thereof.

According to another aspect of the invention a method of controlling patient movements is provided, the method comprising monitoring positions of at least two different body parts of the patient, analyzing the monitored positions to determine, for each body part of the at least two body parts, a displacement of the respective body part with respect to a particular desired position, and providing feedback concerning the displacement of the respective body part.

These and other aspects of the invention are apparent from and will be elucidated with reference to the embodiments described hereinafter.

DETAILED DESCRIPTION OF THE INVENTION

Figure 1:
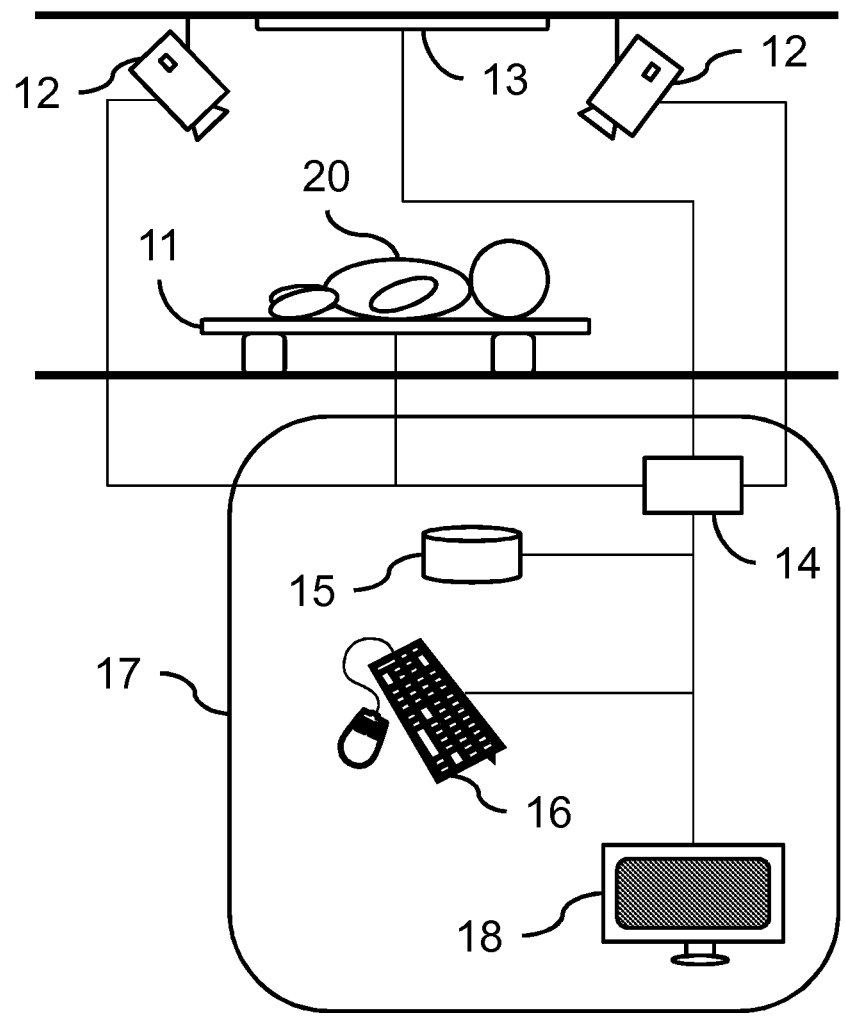
FIG. 1 schematically shows a system for radiotherapeutic treatment.

FIG. 1 schematically shows a system for radiotherapeutic treatment. The system comprises a patient carrier for receiving a patient 20. Here, the patient carrier is a table 11, but other carrier objects like a chair or couch may also be used. Not shown in this schematic picture are the linear accelerator (LINAC) and the LINAC gantry, circling the patient 20 during treatment. The LINAC itself is not shown, because the actual invention does not involve the treatment itself, but only the position and posture of the patient 20 during or in preparation of the treatment. It is to be noted that the same system for controlling the position and posture of the patient may also be useful in other therapeutic and/or diagnostic system, such as MRI, PET or CT scan systems. Furthermore, it is to be noted that the radiotherapeutic system may comprise one or more of such imaging systems.

The system comprises means 12 for monitoring positions of at least two different body parts of the patient 20. In this example, the monitoring means are cameras 12, but many alternative position measuring means may be utilized. For example, pressure or heat sensors in the table may detect contact with the patient 20 or diagnostic imaging tools like MRI, PET and CT scanning equipment may monitor the patient's position and/or posture. Because PET and CT based positioning means is usually already integrated in the LINAC radiotherapeutic system, e.g. for following tumor positions, the use of PET and/or CT scanning equipment for monitoring the position of the different body parts is a very suitable option. Instead of or in addition to monitoring positions, also equipment for measuring movement or velocities of body parts may be used because that is essentially the same as measuring position changes.

The cameras 12 are coupled to a processor 14 of a computer 17 for controlling the motion control system. The computer 17 may be provided as a dedicated computer 17 for realizing the control over the motion and position of the patient 20 or may also serve other purposes, such as controlling the treatment. The computer 17 further comprises a storage means 15 and a user interface 16, which are also coupled to the processor 14. The user interface 16 may comprise input means like a keyboard or pointing device. Preferably, a display screen 18 is provided and also coupled to the processor 14 for providing information about the operation of the system.

The processor 14 is operative to analyze the video data from the cameras 12 and/or input data from other position monitoring means. For this analysis, generally known pattern recognition methods may be used. Body markers may be used for facilitating recognition and location of different body parts. Preferably, input data from multiple different position monitoring means is combined to improve the accuracy of the analysis. The data analysis reveals whether the position of different body parts of the patient 20 is correct and whether these body parts are being moved or kept in position. The raw input data and/or the results of the data analysis may be temporarily or permanently stored on the storage means 15. The position and movements of the patient 20 and different body parts of the patient 20 are then compared to, e.g., desired positions and maximum allowable deviations from the desired positions. When the displacement exceeds a certain threshold, a warning may be provided, indicating that the user should stop moving the corresponding body part. The threshold may only involve a maximum allowable displacement, but may also be a combination of a position and a current direction of movement. When the analysis leads to the conclusion that the deviation is somewhat too large, but the body part is already moving in the right direction, no feedback may be needed at all. Similarly, if the deviation is still within acceptable limits but the body part is moving in the wrong direction, a warning may already be provided. Also a speed of movement of a body part may be determined and compared to a certain allowable margin.

If the analysis shows that the patient position should be corrected, feedback means 13, coupled to the processor 14 are instructed to communicate the need for compensating movements. In this example, the feedback means 13 comprise a display 13 that is visible to the patient 20 lying on the table 11. Alternatively, the display 13 may only be visible to the physician controlling the treatment process and the physician may then provide suitable instructions to the patient 20. Of course, the display 13 may also be visible to both or separate displays 13 may be provided for the patient 20 and the physician. For the physician, the feedback may be shown on the display 18 of the computer 17.

In a preferred embodiment, an ambient experience system is used for providing the feedback. Philips uses an ambient experience system for creating a reassuring environment and reducing anxiety in patients during treatment. The ambient experience system may use, e.g., light, sound and video for creating a pleasant atmosphere. The display means in the ambient experience system may be used for providing the feedback concerning the required compensating movements.

Feedback may also be provided in audible form by one or more speakers or in tactile form, e.g., by vibrating elements positioned at or close to the different body parts (not) to be moved.

Figure 2:
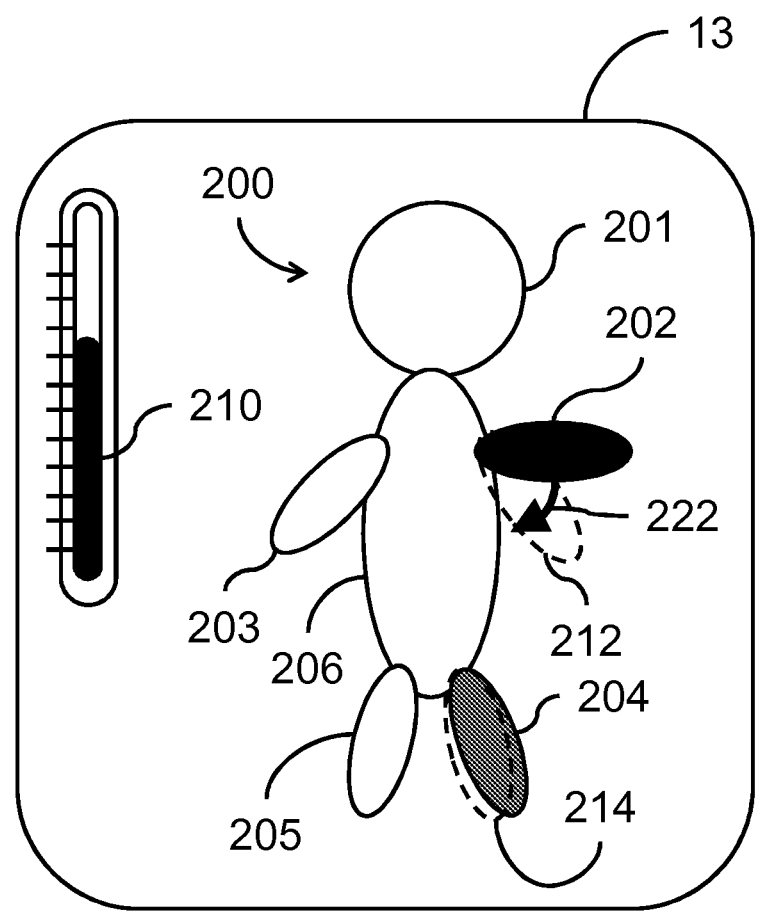
FIG. 2 shows an exemplary image as displayed during use of the system of FIG. 1.

FIG. 2 shows an exemplary image as displayed during use of the system of FIG. 1. The image comprises a schematic representation of the patient 200, divided into six separate body parts 201-206. In the image a head 201, a right arm 202, a left arm 203, a right leg 204, a left leg 205 and a torso 206 are represented. The right arm 202 and the right leg 204 are highlighted for indicating that they are not at their respective desired positions. Color coding may be used for indicating the extent of the displacement. For example, the left arm 202 showing a larger displacement may be colored red and the left leg 204 showing a smaller displacement may be colored orange. The body parts that are in their correct positions may, e.g., be colored green. Optionally, a contour 212, 214 of the incorrectly placed body part in its desired position is displayed to better inform the patient 20 of a required compensating movement. Alternatively, an arrow 222 may indicate the desired direction of movement. A length, width or color of the arrow 222 may indicate the required extent of movement.

The system may also use alternative ways of providing feedback concerning the position and movements of the patient 20. For example, the analysis of the position and movements of the patient 20 may be used to compute a score indicating how well the patient 20 keeps his desired position. The score may continuously be indicated, e.g. as a bar graph 210, to provide an additional incentive for the patient 20 to try not to keep the expected posture. The score may indicate how well the patient 20 is positioned at the current moment, or may provide a cumulative measure of how well he has been positioned during the treatment as a whole. It is to be noted that feedback concerning the position and posture of the patient 20 may also be provided in many other ways.

Figure 3:
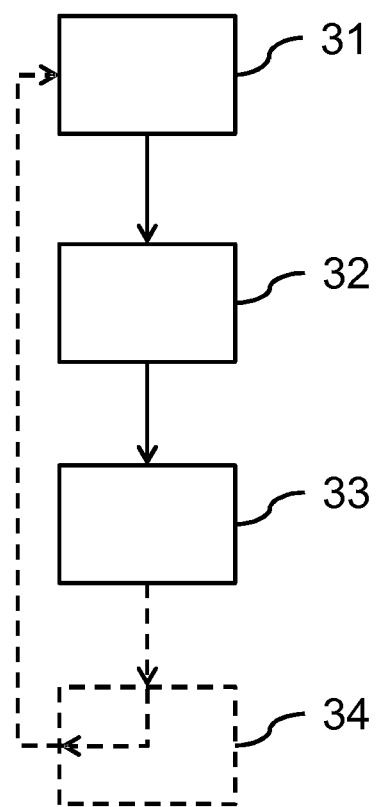
FIG. 3 shows a flow diagram of a method of controlling patient movements.

FIG. 3 shows a flow diagram of a method of controlling patient movements. The method starts with a monitoring step 31 for monitoring movements of at least two different body parts of the patient 20. The monitoring may, e.g., be realized in all the different ways described above with respect to FIG. 1. The monitoring step 31 is followed by an analysis step 32 in which the input data from the monitoring means is analyzed in order to determine whether the patient 20 is in a correct position and posture. For each body part a displacement with respect to a desired position is calculated. In communication step 33, the displacement is communicated to the patient 20 and/or the physician or operator of the system. These three steps are all performed by a system as, e.g., shown in FIGS. 1 and 2. After the feedback is communicated in communication step 33, the patient 20 may move the respective body part in correction step 34 and the monitoring is continued with new feedback messages as result. Also if the patient does not move any body part, the monitoring will be continued.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example processor instructions and/or interpreter instructions (e.g. Java interpreter instructions). Alternatively, one or more or all of the subroutines may be stored in at least one external library file and linked with a main program either statically or dynamically, e.g. at run-time. The main program contains at least one call to at least one of the subroutines. Also, the subroutines may comprise function calls to each other. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth. These instructions may be subdivided into subroutines and/or be stored in one or more files that may be linked statically or dynamically.

The carrier of a computer program may be any entity or device capable of carrying the program. For example, the carrier may include a storage medium, such as a ROM, for example a CD ROM or a semiconductor ROM, or a magnetic recording medium, for example a floppy disc or hard disk. Further the carrier may be a transmissible carrier such as an electrical or optical signal, which may be conveyed via electrical or optical cable or by radio or other means. When the program is embodied in such a signal, the carrier may be constituted by such cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for radiotherapeutic treatment of a patient, the system comprising:
   a patient carrier for receiving the patient,
   means for monitoring positions of at least two different body parts of the patient,
   a processor, coupled to the means for monitoring positions, the processor configured to analyze the monitored positions to determine, for each body part of the at least two body parts, a displacement of the respective body part with respect to a particular desired position, and
   feedback means, coupled to the processor, for interacting with the patient, the feedback means configured to provide feedback to the patient concerning the displacement of the respective body part, the feedback means including a display spaced and positioned relative to the patient carrier to enable the patient to be positioned between the patient carrier and the display,
   wherein the processor is configured to
      (i) determine when an impending displacement of the respective body part with respect to the particular desired position will occur,
      (ii) determine whether the patient typically overcompensates in response to feedback from the feedback means instructing the patient to make a compensating movement of the respective body part, wherein the determination of whether the patient typically overcompensates is based on stored information related to monitored movements of the patient on the patient carrier, and
      (iii) responsive to the determination that the patient typically overcompensates, determine a lesser compensating movement than required to position the respective body part of the patient in the particular desired position, and
   wherein the feedback means are configured to provide the lesser compensating movement to the patient before the impending displacement occurs.

2. A system for radiotherapeutic treatment as claimed in claim 1, wherein the feedback means are configured to move the respective body part in order to undo the displacement.

3. A system for radiotherapeutic treatment as claimed in claim 1, wherein the feedback means are configured to restrict a freedom of movement for the respective body part based on the displacement by raising a dividing wall or inflating air bags of the patient carrier.

4. A system for radiotherapeutic treatment as claimed in claim 1, wherein the processor is further configured to determine a need for the compensating movement of the respective body part and wherein the feedback means are configured to communicate the need for the compensating movement of the respective body part.

5. A system for radiotherapeutic treatment as claimed in claim 4, wherein the processor is further configured to determine a desired direction of the compensating movement and wherein the feedback means are configured to indicate the desired direction.

6. A system for radiotherapeutic treatment as claimed in claim 4, wherein the processor is further configured to determine a desired extent of the compensating movement and wherein the feedback means are configured to indicate the desired extent.

7. A system for radiotherapeutic treatment as claimed in claim 6, wherein the processor is further configured to determine a desired extent of the compensating movement and wherein the display is configured to utilize color coding for indicating the desired extent.

8. A system for radiotherapeutic treatment as claimed in claim 4, wherein the display is configured to display a body representing figure and indicate, for each body part of the at least two body parts, the need for the compensating movement by visually highlighting a respective one of the at least two body parts in the body representing figure.

9. A system for radiotherapeutic treatment as claimed in claim 1, wherein the feedback means are configured to provide visual and/or acoustic feedback.

10. A system for radiotherapeutic treatment as claimed in claim 1, wherein the processor is further configured to determine a score indicating how well the patient keeps an expected posture based on previously monitored positions.

11. A system for radiotherapeutic treatment as claimed in claim 1, wherein the feedback means are configured to provide tactile feedback directly to each body part.

12. A system for radiotherapeutic treatment as claimed in claim 1, wherein the determination of when the impending displacement will occur is based on previously monitored radiotherapeutic treatments of at least one further patient.

13. A method of controlling patient movements with a system including a plurality of cameras, pressure sensors, and/or heat sensors, a processor, and a display, the method comprising:
monitoring, with the plurality of cameras, pressure sensors, and/or heat sensors, positions of at least two different body parts of the patient,
analyzing, with the processor, the monitored positions to determine, for each body part of the at least two body parts, a displacement of the respective body part with respect to a particular desired position,
providing, with the display, feedback to the patient concerning the displacement of the respective body part for informing the patient about the displacement of the respective body part, wherein the display is spaced and positioned relative to the patient carrier to enable the patient to be positioned between the patient carrier and the display,
determining, with the processor, when an impending displacement of the respective body part with respect to the particular desired position will occur,
determining, with the processor, whether the patient typically overcompensates in response to feedback from the feedback means instructing the patient to make a compensating movement of the respective body part, wherein the determination of whether the patient typically overcompensates is based on stored information related to monitored movements of the patient on the patient carrier, and
responsive to the determination that the patient typically overcompensates, determining, with the processor, a lesser compensating movement than required to position the respective body part of the patient in the particular desired position, and
providing, with the display, the lesser compensating movement to the patient before the impending displacement occurs.

14. A method of controlling patient movements as claimed in claim 13, further comprising determining a score indicating how well the patient keeps an expected posture based on previously monitored positions.

15. A computer program product stored on a non-transitory computer-readable medium for use in a method of controlling patient movements, the computer program product configured to cause a processor to perform the method as claimed in claim 13.

16. A system for radiotherapeutic treatment of a patient, the system comprising:
a patient carrier for receiving the patient,
at least one detector configured to monitor positions of at least two different body parts of the patient,
a processor, operatively coupled to the at least one detector, the processor configured to analyze the monitored positions to determine, for each body part of the at least two body parts, a displacement of the respective body part with respect to a particular desired position, and
a display, operatively coupled to the processor, for interacting with the patient, the display configured to provide feedback to the patient concerning the displacement of the respective body part, wherein the display is spaced and positioned relative to the patient carrier to enable the patient to be positioned between the patient carrier and the display,
wherein the processor is configured to
(i) determine when an impending displacement of the respective body part with respect to the particular desired position will occur,
(ii) determine whether the patient typically overcompensates in response to feedback from the feedback means instructing the patient to make a compensating movement of the respective body part, wherein the determination of whether the patient typically overcompensates is based on stored information related to monitored movements of the patient on the patient carrier, and
(iii) responsive to the determination that the patient typically overcompensates, determine a lesser compensating movement than required to position the respective body part of the patient in the particular desired position, and
wherein the display is configured to provide the lesser compensating movement to the patient before the impending displacement occurs.

17. A system for radiotherapeutic treatment as claimed in claim 16, wherein the at least one detector comprises one or more of a camera, a pressure sensor or a heat sensor.

18. A system for radiotherapeutic treatment as claimed in claim 16, wherein the processor is further configured to determine a score indicating how well the patient keeps an expected posture based on previously monitored positions.

* * * * *